United States Patent [19]
de Haan et al.

[11] Patent Number: 5,382,434
[45] Date of Patent: Jan. 17, 1995

[54] LOW STEROID DOSE DRY PHARMACEUTICAL PREPARAITON

[75] Inventors: Pieter de Haan, Oss; M. Deurloo, 's-Hertogenbosch, both of Netherlands

[73] Assignee: Akzo N.V., Arnhem

[21] Appl. No.: 216,236

[22] Filed: Mar. 22, 1994

Related U.S. Application Data

[63] Continuation of Ser. No. 849,921, Mar. 12, 1992, abandoned.

[30] Foreign Application Priority Data

Mar. 12, 1991 [EP] European Pat. Off. ......... 91.200.524

[51] Int. Cl.$^6$ ...................... A61K 9/20; A61K 31/56; A61K 31/585
[52] U.S. Cl. ................................. 424/465; 424/464; 514/169; 514/174; 514/175; 514/960; 514/171
[58] Field of Search ................ 424/464, 465; 514/171, 514/174, 960

[56] References Cited

U.S. PATENT DOCUMENTS

| | | | |
|---|---|---|---|
| 3,423,507 | 1/1969 | Neri et al. | 424/243 |
| 3,568,828 | 3/1971 | Lerner | 206/2 |
| 3,626,063 | 12/1971 | Lincoln et al. | 424/243 |
| 3,671,633 | 6/1972 | Sheth et al. | 424/273 |
| 3,802,914 | 4/1974 | Nezbed | 127/61 |
| 3,957,982 | 5/1976 | Lachnit-Fixson | 424/238 |
| 3,983,233 | 9/1976 | Brattsand et al. | 424/241 |
| 4,143,136 | 3/1979 | DeJager et al. | 424/240 |
| 4,628,051 | 12/1986 | Pasquale | 514/170 |
| 4,916,163 | 4/1990 | Ni | 514/593 |
| 5,006,345 | 4/1991 | Lang | 424/467 |

FOREIGN PATENT DOCUMENTS 0036229  9/1981  European Pat. Off. .

OTHER PUBLICATIONS

"Martindale, The Extra Pharmacopoeia" 28th edition; (1982); p. 54.

J. N. Staniforth, "Advances in Powder Mixing and Segregation in Relation to Pharmaceutical Processing," *Int. J. Pharm. & Prod. Mfr.*, vol. 3 (Suppl.) pp. 1–12, 1982, London, England.

J. N. Staniforth, "Advances in excipient technology Powder and tableting characteristics," *S.T. P. Pharma*, vol. 6, No. 3, pp. 162–168, 1990.

L. S. C. Wan et al., "Incorporation and Distribution of a low dose drug in granules" *International Journal of Pharmaceutics*, 88 (1992) pp. 159–163, no date.

Chase et al., *Remington's Pharmaceutical Sciences*, pp. 1553–1576 (16th ed. 1980, Mack Publ. Co., Easton, Pa., USA.

Thiel et al., "Content Uniformity of microdose Tablets (dosage lug–10 mg) Produced by Fluid Bed Granulation of Interactive Mixtures", *J. Pharmacol.*, 38:335–343 (1986).

Thiel and Nguyen, "Fluidized Bed Granulation of an Ordered Powder Mixture", *J. Pharm. Pharmacol.*, 34:692–699 (1982).

(List continued on next page.)

*Primary Examiner*—Marianne M. Cintins
*Assistant Examiner*—T. J. Criares
*Attorney, Agent, or Firm*—Mary E. Gormley

[57] ABSTRACT

Disclosed are dry pharmaceutical preparations containing potent steroidal medicinal agents in combination with an excipient capable of binding the agent to an extent greater than 80% and a having a demixing potential of less than 10% for said agent. Such excipients include spray-dried polyalcohols, granulated α-lactose monohydrate, or mixtures thereof. Also disclosed is a process of manufacturing stable tablets containing nearly identical amounts of at least one steroidal medicinal agent present in each tablet in an amount varying from 0.005 to 0.5 percent by weight of the tablet. Also disclosed is a dry mix consisting essentially of 1 to 100 parts, by weight, of at least one medicinal agent uniformly distributed throughout 2000 to 20,000 parts, by weight, of the described excipients. The mixture can be used to make dry dosage forms such as capsules, tablets, powders, and slugged granulates.

18 Claims, 4 Drawing Sheets

OTHER PUBLICATIONS

Thiel et al. "Fluidised Bed Granulation of an Ordered Powder Mixture Reduces the Potential for Ordered Unit Segregation", *Powder Technology*, 34:75–80 (1983).

Nikolakakis & Newton, "Solid State Adsorption of Antibiotics onto Sorbiton" *J. Pharm. Pharmacol.*, 41:145–148 (1989).

Schmidt & Benke, "Ubersattigte Geordnete Mischungen auf der Basis von Sorbit", *Pharm. ind.*, 46(2):193–198 (1984).

Cartillier and Moes, "Influence dy Type de Lactose sur Cohesif et Faiblement Dose", *S.T.P. Pharma*, 5(3):152–159 (1989).

LOW STEROID DOSE DRY PHARMACEUTICAL PREPARAITON

This is a continuation of application Ser. No. 07/849,921 filed Mar. 12, 1992, now abandoned.

TECHNICAL FIELD

This invention relates to pharmaceutical compositions generally, and more specifically to dry mixtures, tablets, pills or granulates containing potent steroid compounds.

BACKGROUND ART

Methods for making tablets and other solid or dry pharmaceutical preparations are well-known. For example in the well-known English language text Chase, et al, *Remington's Pharmaceutical Sciences*, pp. 1553–1576 (16th ed. 1980, Mack Publ. Co. of Easton, Pa., U.S.A.) ("*Remington's*"), methods of making tablets, capsules and pills and their respective components are described.

Three methods of making tablets include the "wet-granulation", "dry-granulation", and direct compression methods.

Wet-granulation methods involve weighing out ingredients (including a solvent), mixing the ingredients, granulating them, screening them damp, drying them, dry screening, lubrication, and compressing the resultant admixture into tablets. See, e.g. Belgian Patent No. 773,064. Such procedures result in tablets having at least adequate tablet homogeneity. Wet-granulation methods may have a disadvantage when certain solvents, which may not be desired in view of environmental and safety concerns, are used.

The dry methods (dry-granulation and direct compression) are especially suitable for medicinal compounds which are sensitive to moisture or are unable to withstand the elevated drying temperatures associated with wet-granulation methods.

Dry granulation methods involve fewer steps (i.e. weighing, mixing, slugging, dry screening, lubrication and compression), while direct compression methods lack the slugging and, usually, the dry screening steps. However, these dry methods have heretofore not been entirely successful in providing optimal tablet homogeneity when used with certain very potent medicinal compounds. For example, compounds such as certain extremely potent steroids require only very low doses of the compound per tablet (e.g. <1.0 milligrams (mg)/100 mg tablet) and do not always distribute entirely evenly throughout a tableting mixture possibly resulting in some tablets having relatively high amounts of steroid (i.e. "superpotent tablets"), while others have very low amounts of steroid or possibly none at all.

A common diluent used with both wet and dry granulating processes is lactose. Different types or lactose are commercially available. There are $\alpha$-lactose monohydrate, $\beta$-lactose (also known as "anhydrous lactose DT", and used in direct compression methods), anhydrous lactose, and spray-dried lactose (see, e.g. *Martindales' The Extra Pharmacopoeia*, p. 54 (The Pharmaceutical Press, London 28th ed. 1982).

Certain types of lactose have been used with low dose steroids to make tablets. For example in U.S. Pat. No. 4,628,051 to Pasquale, compositions containing anhydrous lactose DT (i.e. $\beta$-lactose) and low dose steroids are disclosed. The disclosed compositions when used in a dry procedure produce tablets of inadequate homogeneity (see e.g. EXAMPLE II, infra). Similar compositions are disclosed in U.S. Pat. Nos. 4,544,554, 4,616,006, and 4,530,839 also to Pasquale Other tablet compositions containing lactose and a low dose steroid are described in the art. However, by including polyvinylpyrrolidone ("PVP"), stearic acid, or other ingredients exclusively used in wet-granulation processes in the formula for the preparations, one of skill in the art can readily determine that a wet-granulation procedure was used in forming the tablets. Such compositions are disclosed in U.S. Pat. Nos. 3,939,264, 3,969,502, and 3,957,982 to Lachnit-Fixson, U.S. Pat. No. 4,425,339 to Pitchford, U.S. Pat. No. 4,390,531 to Edgren, U.S. Pat. No. 3,822,355 to Biological Concepts, Inc., U.S. Pat. Nos. 4,378,356 and 4,143,136 to De Jager et al (stearic acid).

U.S. Pat. No. 3,671,633 to Sheth discloses a process of making acetazolamide tablets which does not require prior granulation or slugging to obtain commercially acceptable tablets. The process uses crystalline acetazolamide having a binodal size distribution mixed with, for example, 30 to 80 weight percent spray-dried lactose. Dosages of acetazolamide are typically 500 milligrams per tablet, so none of the problems associated with extremely potent drugs are encountered.

U.S. Pat. No. 4,916,163 to Ni discloses formulations of the non-steroid sulfonylurea glyburide having improved bioavailability consisting preponderantly (>70%) of spray-dried lactose with a relatively narrow sieve fraction. Tablets disclosed contain micronized glyburide having a surface area of at least 3 $m^2/g$.

Tablet compositions containing steroids in combination with spray-dried lactose are also disclosed. For example U.S. Pat. No. 3,568,828 to Werner discloses oral contraceptive tablets made by mixing mestranol and chlormadinone in chloroform, adding microcrystalline cellulose to the solution, drying the mixture, and then blending the dried mixture with spray-dried lactose before compressing the blend into tablets. Although the mestranol and chlormadinone may be evenly distributed on the cellulose, the procedure still utilizes chloroform which is undesirable from environmental and safety view points.

U.S. Pat. No. 3,423,507 describes dry pharmaceutical formulations containing between 1.5 and 12.5 percent steroid by weight. In the preparation of the tablet formulations, the steroid is first mixed with an equal amount of starch, before blending with spray dried lactose. However as shown in EXAMPLE IV, infra, premixing a starch with an ultra-low dose steroid before blending with the spray-dried polyalcohol (SAMPLE 2) results in a dry mix having significantly lower content uniformity than mixtures wherein the steroid is first mixed with the spray-dried polyalcohol.

Compositions containing microdose quantities of a micronized model drug (salicylic acid, due to it low aqueous solubility and its hydrophobicity) and spray-dried lactose have been further used in wet granulation techniques to produce tablets having good homogeneity. Thiel et al, "Content uniformity of microdose tablets (dosage 1 $\mu$g–10 mg) produced by fluid bed granulation of interactive mixtures", *J. Pharm. Pharmacol*, 38: 335–343 (1986); Thiel and Nguyen, "Fluidized bed granulation of an ordered powder mixture", *J. Pharm. Pharmacol.*, 34: 692–699 (1982); and Thiel et al "Fluidised bed granulation of an Ordered Powder Mixture Reduces the Potential for Ordered Unit Segregation", Powder Technology, 34: 75–80 (1983). The demixing potential of the model drug when mixed with spray-dried lactose sans the application of a wet granulation technique was 70 to 80%. By the use of a wet granulation technique (5% aqueous solution of PVP) the demixing potential was reduced to 5.6 to 10.8%.

SUMMARY OF THE INVENTION

It has now been found that by dry mixing steroidal medicinal agents with excipients having a demixing potential of less than 10% and a binding affinity of greater than 80 percentage bound for these agents, a process results having surprisingly good properties with regard to robustness and ruggedness, while the resulting dry mixtures are very homogenous with regard to content uniformity even with very potent steroids.

The invention thus includes dry pharmaceutical preparations containing ultra-low doses of one or more micronized steroidal medicinal agents in combination with a primary excipient having a high binding affinity and low demixing potential for the steroidal medicinal agent. Such excipients include spray-dried polyalcohols, granulated $\alpha$-lactose monohydrate (essentially 100% lactose), and mixtures thereof. As used herein, a steroidal medicinal agent is one having a chemical structure containing a cyclopentanoperhydrophenanthrene backbone.

The invention also includes a process of manufacturing stable, uniform tablets containing nearly identical amounts of at least one steroidal medicinal agent present in each tablet in an amount varying from 0.005 to 0.5 percent by weight of the tablet. The process to make such tablets includes: dry mixing 1 to 100 parts, by weight, of at least one medicinal agent with 2000 to 20,000 parts, by weight, with the described primary excipient. If needed, further excipients, in an amount of up to nine times the weight of the medicinal agent/lactose mixture may be mixed with the mixture to form an admixture containing 0.005 to 0.5% medicinal agent by weight with the remainder being spray-dried polyalcohol, granulated $\alpha$-lactose monohydrate, further excipients, or mixtures thereof. Finally the resulting mixture is compressed into tablets containing less than 0.5 percent steroidal medicinal agent by weight.

The invention thus further includes a dry mix consisting essentially of 1 to 100 parts, by weight, of at least one steroidal medicinal agent uniformly distributed throughout 2000 to 20,000 parts, by weight, of a primary excipient selected from the group consisting of spray-dried polyalcohols, granulated $\alpha$-lactose monohydrate, and mixtures thereof. This dry mix is, if it is not already in the described proportions, then mixed with further excipients to form an admixture containing from 0.005 to 0.5 percent steroid by weight and from 99.5 to 99.995 percent selected polyalcohol and further excipients, by weight. These further excipients are either the same excipient as originally used, or may be other drugs or other excipients commonly used in tableting (e.g. $\beta$-lactose or starch). A mixture having the described proportions can be used to make dry dosage forms such as capsules, tablets, powders, and slugged granulates.

The described processes are free from organic solvents which may not be desired for safety, environmental, and economic reasons. Non-use of organic solvents further eliminates the risk that such solvents can be accidentally released into the environment. The non-use of flammable organic solvents (e.g. ethanol or acetone) also decreases the chance of worker injury. Furthermore, the lack of solvents tends to preserve the crystalline structure of the lactose and active ingredients, making the resulting dosage forms easier to handle and manufacture. The resulting tablets have enhanced dissolution rates.

Another advantage of the invention is that the micronized active ingredients are tightly bound and evenly distributed over different size sieve fractions of the granulate. Since the resulting process results in a homogenous mixture for tableting, there is less waste attributable to superpotent or hypopotent dry mixtures. The resulting tableting mixture is less troublesome with regard to variations in content of active ingredients in the tablets during the tableting process. The process is thus more "rugged" or "robust" with regard to content uniformity having fewer "hot" (i.e. an area having too much steroid) and "cold" (i.e. an area having too little steroid) spots in the tableting mixture. As used herein, "robust" or "rugged" means that typical changes in process variables (e.g. mixing time, batch size, and tableting speed) do not significantly adversely affect the resulting product.

Furthermore, during processing, constituent segregation (e.g. steroid from primary excipient) is minimalized due to the high binding affinity of the steroid for the excipient. Also because of the low demixing potential, the adhesive unit segregation (i.e. the segregation of different sized excipient particles that occurs during processing) does not affect the homogeneity of the resulting dosage units since an even distribution of steroid over various sieve fractions results.

Another advantage of the invention is its ability to be mixed with further other excipients which may be desired for various reasons (e.g. improved ability to inscribe the tablet with a punch, the ability to use lower cost excipients, decrease the fragility of the resulting tablets, etc.).

The inventive mixtures also have a high physical stability with regard to content uniformity even under extreme segregating conditions. This stability applies to handling, storage and transport of the dry mix.

DETAILED DESCRIPTION OF THE INVENTION

Figure 1:
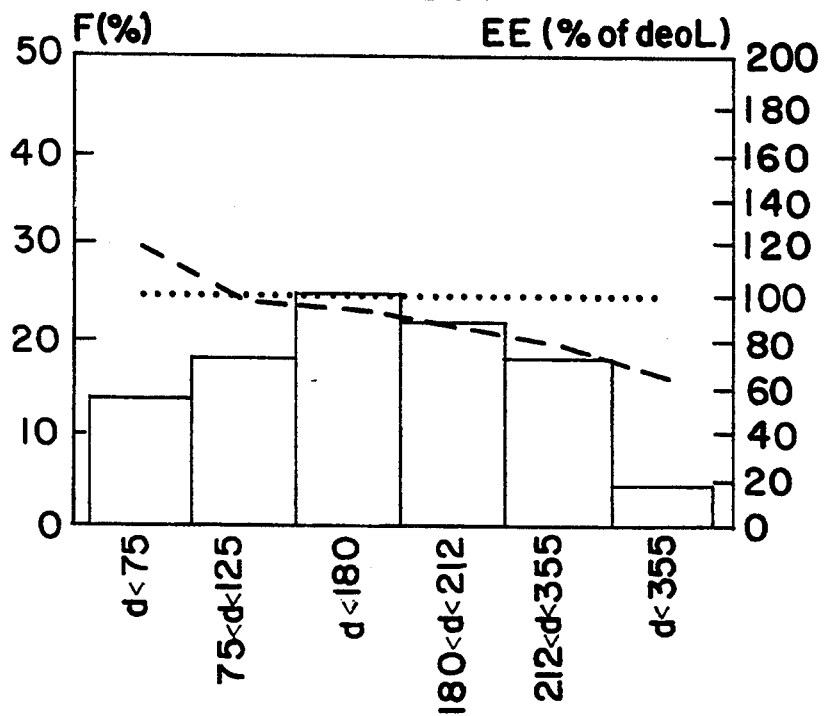
FIGS. 1 to 4 show the relative distribution of a low dose component (0.05% EE w/w) among various sieve fractions of granulated $\alpha$-lactose monohydrate, $\beta$-lactose, spray-dried lactose, and crystalline $\alpha$-lactose monohydrate respectively.
Figure 2:
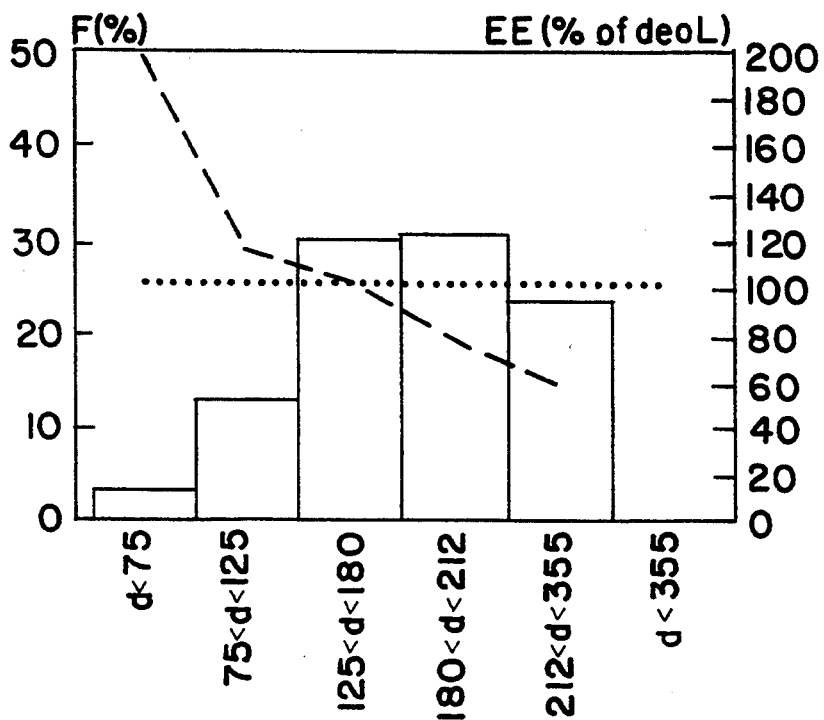
Figure 3:
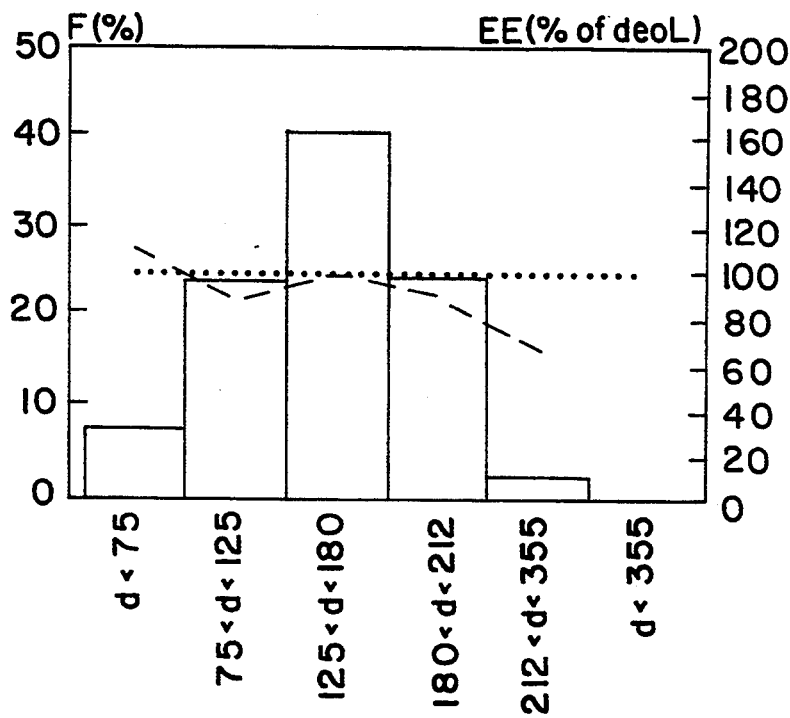
Figure 4:
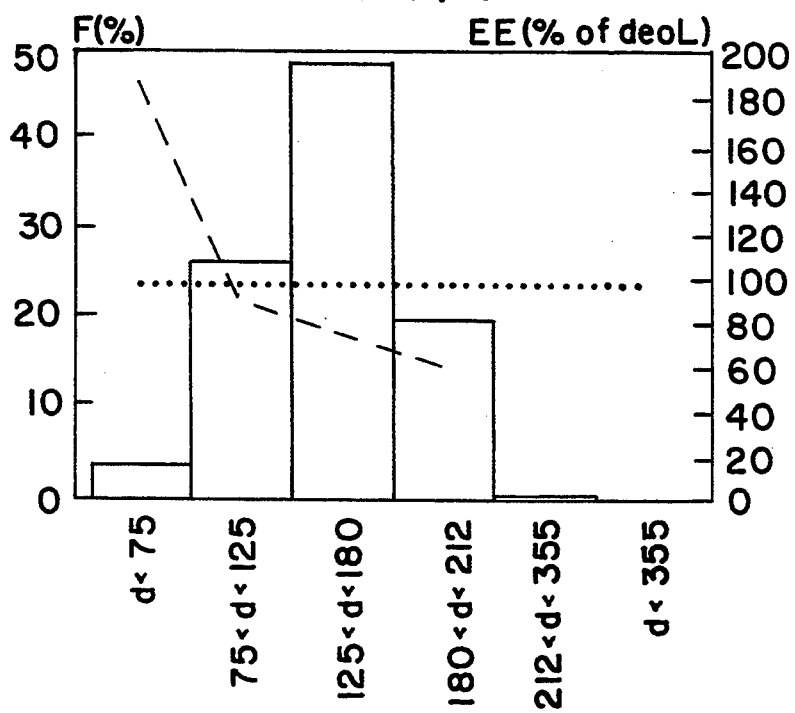
Figure 5:
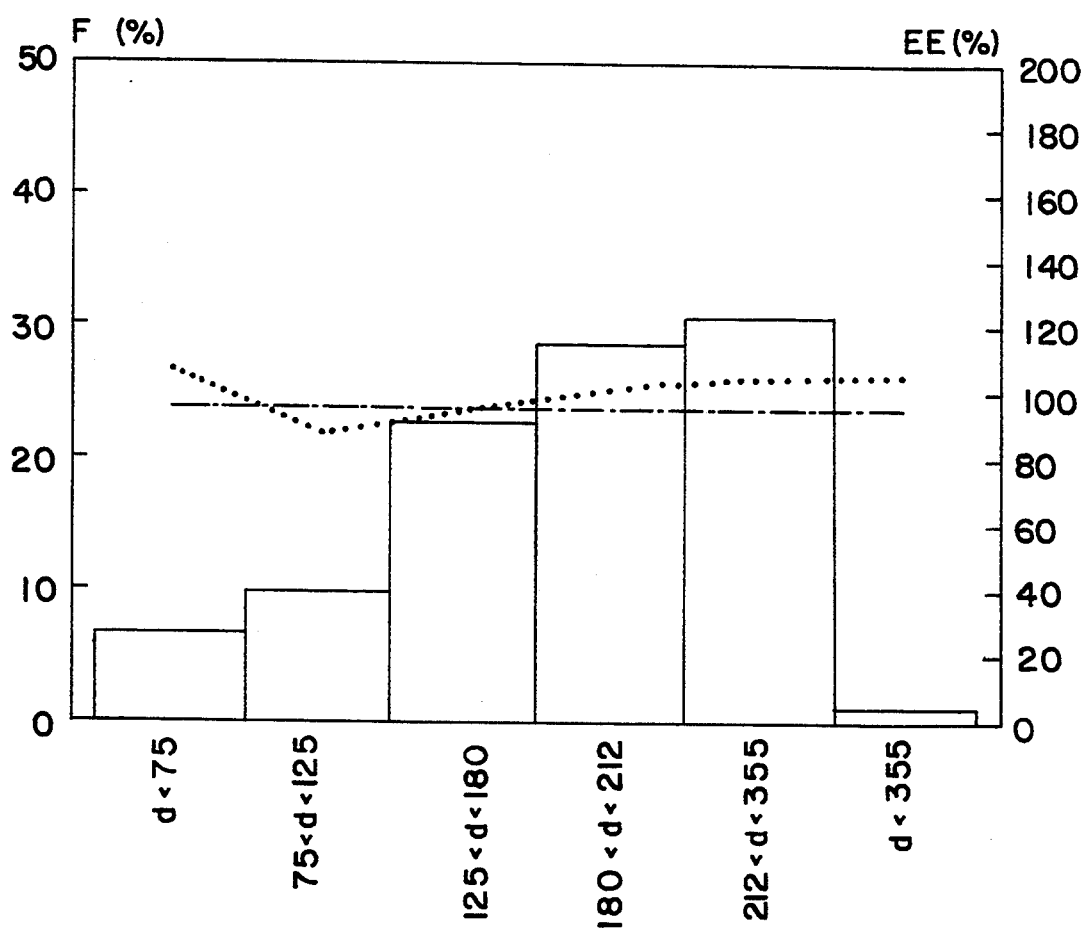
FIG. 5 depicts the distribution of ethinyl estradiol (0.05% EE w/w) over different sieve fractions of a spray-dried combination product consisting of the polyalcohols lactose (75%) and cellulose (25%).

The stable dry pharmaceutical preparation is preferably a tablet, capsule, pill, or powder. Tablets are the presently most preferred preparation.

Various low dose steroidal medicinal agents can be used with the invention, however typical of such medicines are certain potent steroids, digoxin, and digitoxin. Medicinal agents such as digoxin and digitoxin, although not "steroids" in the classic pharmacologic sense, have a "steroid backbone" and thus are included within the scope of the invention. The medicinal agents may be micronized by conventional (e.g. by air milling, ball milling, and crystallization) techniques.

Steroids used in the compositions and processes of the invention are preferably estrogens, progestogens, or both of them.

Preferred progestogens for use with the invention include 3-ketodesogestrel ("etonogestrel"), desogestrel, levo-norgestrel, norgestrel, gestodene, and other compounds with similar progestogenic activity. Especially preferred are 3-ketodesogestrel and desogestrel.

Examples of preferred estrogens include ethinyl estradiol, mestranol and 17-α-ethinyl estradiol 3-methylether. Especially preferred is ethinyl estradiol.

Various medicinal agents have various acid addition salts which may effect their potency. Acid addition salts are derived from pharmaceutically acceptable acids, such as hydrochloric acid, sulfuric acid, phosphoric acid, acetic acid propionic acid, glycolic acid, maleic acid, fumaric acid, malonic acid, succinic acid, tartaric acid, lactic acid, citric acid, ascorbic acid, benzoic acid, methanesulfonic acid and the like.

The term "dosage unit" or "pharmaceutical dosage unit" generally refers to physically discrete units suitable as unitary dosages for humans or animals, each containing a predetermined quantity of active material (e.g. estrogen or progestogen) calculated to produce the desired effect. Examples of such dosage units are tablets, capsules, powders, and pills.

The amount of medicinal agent in a dosage unit will of course depend on the potency of the particular agent and its intended use. The amount of a medicinal agent used in a dosage unit will be well-known to those skilled in the art, and may depend on the particular acid addition salt used. As an approximation, levonorgestrel, desogestrel, and 3-ketodesogestrel are relatively equipotent, in progestogenic activity. Gestodene is approximately 1.5 times as potent as these compounds orally. Norgestrel is about one-half as potent as levonorgestrel. As an approximation, 0.015 mg of ethinyl estradiol is equivalent in estrogenic activity to 0.030 mg of mestranol.

Primary excipients for use in the invention have a high binding affinity (with greater than 80% of the steroid bound to the excipient) and a low demixing potential (<10%) for the particular steroidal medicinal agent. Especially preferred excipients bind to the steroidal medicinal agents in amounts greater than 90%, and have a demixing potential of less than 7.5%. They will also preferably possess low friability (decreased incidence of particle attrition due to normal dry mixing process conditions.

Demixing potential (DP %) may be calculated by the following formula:

$$DP\% = \frac{100}{\bar{p}} \left[ \sum_{i=1}^{n} \frac{w_i}{100} (p_i - \bar{p})^2 \right]^{\frac{1}{2}}$$

wherein $p_i$ is the proportion of drug associated with $w_i$ weight % of the mixture in sieve fraction i. The mean composition may be determined by:

$$\bar{p} = \frac{\sum_{i=1}^{n} p_i * w_i}{\sum_{i=1}^{n} w_i}$$

Determination of the percentage of a drug bound to an excipient can be readily measured by one of skill in the art. See, e.g. Nikolakakis & Newton, "Solid State Adsorption of Antibiotics onto Sorbitol", *J. Pharm. Pharmacol.*, 41: 145–148 (1989) and references cited therein, and Schmidt & Benke, "'Übersättigte' geordnete Mischungen auf der Basis von Sorbit", *Pharm. Ind.*, 46(2): 193–198 (1984). This process is used in conjunction with a quantitative analysis technique such as HPLC with fluorimetry detection, to measure the percentage of steroid bound to the particle after dry-mixing.

Preferred primary excipients for use in the invention are spray-dried polyalcohols, especially spray-dried lactose and spray dried combinations of lactose and cellulose (e.g. Cellactose, which is 75% lactose and 25% cellulose available from Meggle Milchindustrie GmbH & Co. KG of Wasserburg, Germany). Other spray dried poly-alcohols include spray-dried mannitol, sorbitol, cellulose, xylitol, dextrose, fructose, and sucrose. As used herein, spray-drying should not be confused with "spray-crystallization" such as that used by the Finnish Sugar Co., Ltd. of Carmel, N.Y. for producing Empdex dextrates.

A preferred spray-dried polyalcohol for use in the invention is spray-dried lactose. The presently most preferred lactoses for use in the invention are commercially available under the trade designations Pharmatose DCL-11 (DMV Campina, bv, Veghel, NL), and Fast Flo 316 (Foremost, USA).

Although not required for making dosage units according to the invention, the use of conventional additives or "further excipients", e.g. colorants, disintegrants, lubricants, glidants, fillers, binders, and the like is contemplated. Typical examples of such excipients are microcrystalline cellulose, crystalline lactose, colloidal silicon dioxide, and directly compressible starches. Stabilizers such as EDTA, polyethylene glycol (PEG), butylated hydroxy toluene (BHT), and α-tocopherol may also be included if desired, although it is not required. Other medicinal agents (e.g. 17β-estradiol may also be included in the formulation so long as the primary excipient is first used to distribute the extremely potent steroidal agent evenly through the dry mixture, and the potent steroidal agent is in the end mixture in an amount less 0.5 percent by weight. Furthermore, after compression, the tablets may be coated.

As an added feature of the invention, the resulting tablets are surprisingly chemically stable (even without added stabilizers) to temperature and humidity changes.

A preferred method according to the invention involves dry mixing one part to 100 parts of the particular medicinal agent chosen with 2000 parts to 20,00 parts of lactose (spray-dried lactose, granulated α-lactose monohydrate, or a mixture thereof) until a uniform (<6% RSD) mixture ("dry mix") is achieved as may be determined by sampling randomly selected dosage units may from that mixture. This uniform mixture is either used as it then exists, i.e. if it has a content of medicinal agent of 0.005 to 0.5% by weight, or it may be further mixed with up to nine times its weight of further different excipients until its content of medicinal agent is between 0.005 to 0.5% by weight. The mixture may then be tabletted or encapsulated by means well-known to those skilled in the art.

The uniformity of the dry mixing process or dosage units made therefrom can be determined by taking representative samples of the mixture or dosage units to be tested, and quantitatively analyzing (e.g. by HPLC) the samples for content of medicinal agent. Methods for determining content uniformity of the samples are known, but a preferred method is described in *USP XXII*, "<905> Uniformity of Dosage Units" at pages 1617–1619. The *USP XXII* describes content uniformity tests for both a maximum and minimum value for the content of individual samples and a relative standard deviation of the total set of samples. Using the method of the invention, the mixture is preferably mixed until a content uniformity (relative standard deviation) of ±1.5 percent, preferably ±1 percent, and most preferably ±0.5 percent (w/w) is achieved.

Methods and compositions for making various dosage units using the uniform dry mix are well-known to those skilled in the art. For example, methods and compositions for making tablets, capsules and pills are described in *Remington's*, at pages 1553 through 1584. Methods of using powders, and their composition are described at pages 1535 through 1552 of the reference. Methods of coating pharmaceutical dosage units are described at pages 1585 to 1593 of *Remington's*.

Due to the binding properties of the excipients, little or no medicinal agent is found to be lost when the dry mixture is passed over a metal surface (e.g. a mixing apparatus, a sieve or a tableting machine).

The invention is further explained by reference to the following illustrative examples:

EXAMPLE I

Tablets containing:

| | |
|---|---|
| Desogestrel (micronized) | 150 μg |
| EE (micronized) | 30 μg |
| Na starch glycolate | 1.2 mg |
| Colloidal SiO$_2$ | 0.9 mg |
| Mg Stearate | 0.3 mg |
| Pharmatose DCL-11 qsad | 60.0 mg | were made. The tablets were made by first dry mixing the medicinal agents (desogestrel and EE) with suitable quantities of spray dried lactose for approx. 3 min. The other ingredients were then also mixed into the mixture until for approx. 5 min. The mixture was then tabletted by direct compression. The tablets contained within ±2.5% (w/w) of the stated amount of steroids.

EXAMPLE II

Different types of the polyalcohol lactose were tested for their ability to be used with extremely low doses of steroids. Four different samples containing micronized EE (0.05% w/w) were made using:
a) granulated α-lactose monohydrate for direct compression (Tablettose (TM) from Meggle),
b) anhydrous lactose DT (Pharmatose DCL-21 (TM) from DMV),
c) spray dried lactose for direct compression (Pharmatose DCL-11),
d) crystalline α-lactose monohydrate (Pharmatose M100 from DMV) respectively, and
e) a direct compression vehicle consisting of spray-dried 75% lactose and 25% cellulose (Cellactose-Meggle).

As depicted in FIGS. 1 to 5, Samples a, c and e resulted in an even distribution of the low dose of active ingredient over different sieve fractions. Samples b and d however resulted in a distribution of the low dose of active ingredient with higher concentrations of EE in the smaller sieve fractions.

EXAMPLE III

Ten grams of ethinylestradiol and 50 grams of desogestrel are dry mixed with 19.440 kilograms of spray dried lactose (Pharmatose DCL 11). After mixing, 400 grams of sodium starch glycolate and 100 grams of magnesium stearate are incorporated into the mixture. The resulting mixture is then divided into halves, half of which is used to make 100 mg direct compression tablets, and the other half is used to make capsules. The tablets are tested for content uniformity as described in *XXII*, "<905> Uniformity of Dosage Units" at pages 1617–1619. The results show that the desogestrel and the EE are evenly distributed throughout the tablets. Similar tests on the capsules provide results showing even distribution of desogestrel throughout the powdered mixture.

EXAMPLE IV

SAMPLE 1. A dry mix sample containing only 0.05% by weight micronized ethinylestradiol ("EE"), obtained from Diosynth bv (Oss, NL), and the remainder spray dried lactose (Pharmatose DCL-11) was made by mixing the lactose with the EE for 2.5 mins.

SAMPLE 2. A dry mix sample was also made containing 0.05% (w/w) micronized EE, 2.00% sodium starch glycolate (Primojel), and DCL-11 lactose (qsad 100%). Primojel is a essentially a modified starch product with similar particle size and other properties as starch. The DCL-11 was pre-blended with the Primojel, to which the EE was added, and mixed for 7.5 minutes.

SAMPLE 3. A dry mix sample was also made containing 0.05% (w/w) micronized EE, 2.00% sodium starch glycolate (Primojel), and DCL-11 lactose (qsad 100%). However in this case, the DCL-11 was pre-blended with the EE for 2.5 minutes, to which the Primojel was added, and mixed for another 5 mins.

Tablets were prepared from each of the SAMPLEs. Tablets having a diameter of 5 mm and a mass of 60 mg were compressed on a rotary press. Tablets were sampled at different times during the process, and analyzed for EE content.

Testing:

Each of the three sample tablets was tested on reverse phase HPLC to determine the content uniformity of various samples. The samples were disintegrated, dissolved into a standardized estradiol solution, and centrifuged. The supernatant was analyzed on HPLC-equipment (Waters-Millipore) equipped with a Novapak C18 column. Detection of EE was carried out by fluorimetry at 205 nm/300 nm.

Data Analysis:

Normalized EE contents were calculated from the weight (WGHT) and corresponding EE content (EE) of each sample according to the formula:

$$NORM\ EE = \frac{EE_s * WGHT_r}{WGHT_s * EE_r} * 100\%$$

in which s and r refer to sample and reference respectively. The average normalized content and relative standard deviation (RSD) were then calculated for the samples and compared with theoretical values calculated according to Johnson, MCR "Particle size distribution of the active ingredient for solid dosage forms of low dosage", Pharm. Acta Helv., 47: 546–559 (1972). A Chi-squared test was used for determining statistical significance.

Results:

All batches of Samples 1 and 3 were nearly identical in having content uniformity as good as theoretical values (±0.5%). All batches of Sample 2 however were of significantly ($p<0.05$) lower quality with regard to content uniformity, even though a longer mixing time was used.

EXAMPLE V

The procedures of EXAMPLE III are repeated, except using 12.5 mg of digoxin and 9.875 grams (in total) spray-dried lactose. 100 tablets, each containing 125 µg of digoxin are made by direct compression of the dry mixture.

EXAMPLE VI

The binding affinity and demixing potential of various excipients vis-à-vis micronized ethinylestradiol were investigated. EE (0.05% w/w) was dry mixed with:
a) spray dried lactose (Fast Flo 316),
b) spray dried lactose/cellulose 75:25 (Cellactose),
c) spray dried lactose (Pharmatose DCL-11),
d) granulated α-lactose monohydrate (Tablettose),
e) microcrystalline cellulose (Avicel PH101),
f) microcrystalline cellulose (Avicel PH102),
g) granulated rice starch,
h) granulated lactose/potato starch/PVP,
i) spray-crystallized dextrates (NF XVI) (Emdex ™ Finnish Sugar Co., Ltd.),
j) β-lactose (Pharmatose DCL-21),
k) granulated lactose/corn starch/PVP, and
l) crystalline α-lactose monohydrate (Pharmatose M100).

Mixtures were then sieved over a 45 µm sieve on an Alpine Air Siever. The concentrations of EE associated with the mixture were determined before and after sieving by use of HPLC with fluorimetry detection. The percentage of EE bound to the various excipients was determined for each of the twelve samples, as was the maximum, minimum, difference, and demixing potential.

| PERCENTAGE BINDING AFTER ALPINE STRESS TESTING | | | | | |
|---|---|---|---|---|---|
| Excipient | % Bound | Max. | Min. | Diff. | DP % |
| a | 96.7 | 104.7 | 100.7 | 4 | 1.6 |
| b | 89.8 | 100.7 | 83 | 17.7 | 5.8 |
| c | 97.4 | 104.5 | 71.2 | 33.3 | 7.4 |
| d | 83.5 | 94.8 | 67 | 27.8 | 6.4 |
| e | 55 | 96 | 78 | 18 | 9.4 |
| f | 63.5 | 132.3 | 74 | 58.3 | 23.9 |
| g | 80.3 | 154.9 | 86.1 | 68.8 | 20.7 |
| h | 88.4 | 201.2 | 66.3 | 134.9 | 22.4 |
| i | 82.5 | 163.3 | 25.2 | 138.1 | 39 |

| PERCENTAGE BINDING AFTER ALPINE STRESS TESTING -continued | | | | | |
|---|---|---|---|---|---|
| Excipient | % Bound | Max. | Min. | Diff. | DP % |
| j | 61.4 | 205.5 | 51.9 | 153.6 | 55 |
| k | 70.6 | 221.1 | 57.6 | 163.5 | 38.9 |
| l | 64.7 | 240.8 | 57 | 183.8 | 51.4 |

Figure 6:
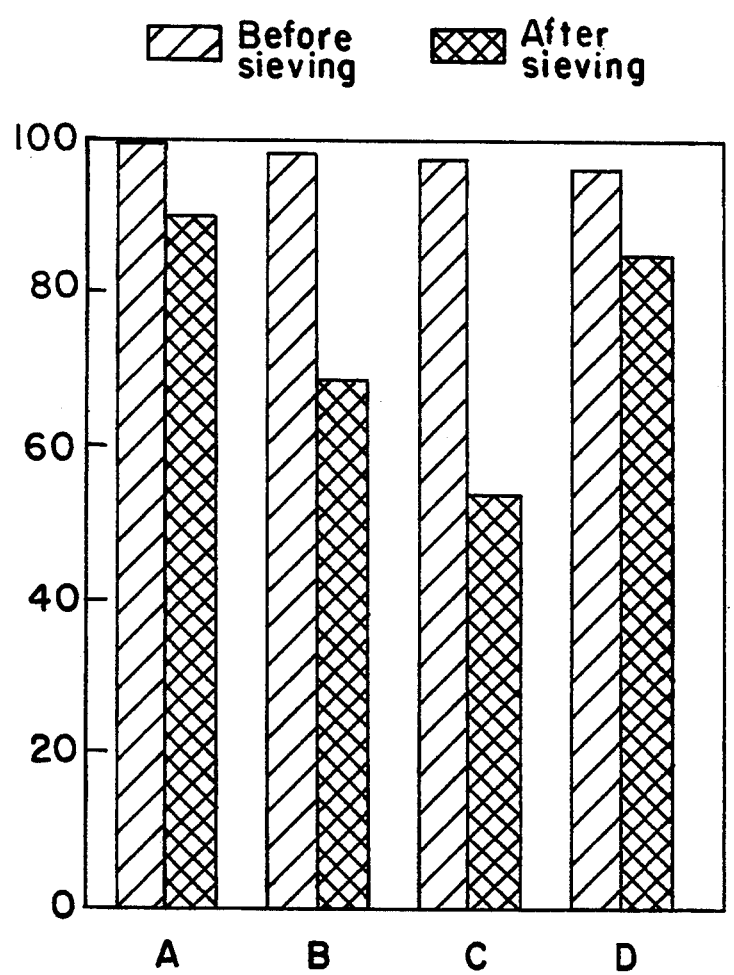
FIG. 6 depicts the results of a stress test on the stability of various compositions using (A) spray-dried lactose, (B) $\beta$-lactose, (C) crystalline $\alpha$-lactose monohydrate, and (D) granulated $\alpha$-lactose monohydrate.

As depicted in FIG. 6, both spray dried lactose and granulated α-lactose monohydrate lost less of the associated EE upon sieving and showed superior binding of the drug particles associated with the carrier. Moreover, superior distribution of the active compound over the sieve fraction was found. With this stress test on segregation the phenomenon of superior stability of compositions using the selected excipients in combination with the ultra-low dose steroid is demonstrated.

EXAMPLE VII

Preliminary in vitro dissolution studies were conducted comparing the tablets of EXAMPLE I with desogestrel containing tablets such as those described in the third phase of Example VIII of EP-A-0 036 229 (corresponding to U.S. Pat. No. 4,378,356 to de Jager). The tablets were placed into an aqueous 0.1% sodium dodecyl sulfate solution, and the time required for the tablets to dissolve was measured.

In the procedure 52% of the desogestrel dissolved into the solution after 15 mins. from the prior art tablets versus 84% from tablets of EXAMPLE I.

EXAMPLE VIII

The following tablets are made using a dry mix process according to the invention:

| Compound | Amount (mg/tablet) |
|---|---|
| A. | |
| ethinyl estradiol | 0.025 |
| 3-ketodesogestrel | 0.100 |
| Na starch glycolate | 1.2 |
| Colloidal SiO$_2$ | 0.9 |
| Mg Stearate | 0.3 |
| Cellactose qsad | 60.0 |
| B. | |
| ethinyl estradiol | 0.020 |
| desogestrel | 0.125 |
| Na starch glycolate | 1.2 |
| Colloidal SiO$_2$ | 0.9 |
| Mg Stearate | 0.3 |
| spray-dried lactose qsad | 60.0 |
| C. | |
| ethinyl estradiol | 0.020 |
| desogestrel | 0.150 |
| Na starch glycolate | 1.2 |
| Colloidal SiO$_2$ | 0.9 |
| Mg Stearate | 0.3 |
| granulated α-lactose mono-H$_2$O qsad | 60.0 |
| D. | |
| desogestrel | 0.035 |
| Mg Stearate | 0.3 |
| Colloidal SiO$_2$ | 0.9 |
| spray-dried lactose qsad | 60.0 |

References herein to specific Examples or embodiments should not be interpreted as limitations to the extent of protection which shall be determined by the terms of the claims.

What is claimed is:

1. A pharmaceutical dosage unit consisting essentially of 1 to 100 parts, by weight, of at least one steroidal medicinal agent uniformly distributed throughout 2000 to 20,000 parts, by weight, of an excipient capable of binding said steroidal medicinal agent to an extent greater than 80% and a demixing potential of less than 10% for said steroidal medicinal agent, in the form of tablets, capsules or slugged granulates.

2. The pharmaceutical dosage unit of claim 1 wherein said medicinal agent is selected from desogestrel, 3-ketodesogestrel, ethinylestradiol, gestodene, or mixtures thereof.

3. A pharmaceutical dosage unit consisting essentially of 1 to 100 parts, by weight, of at least one steroidal medicinal agent uniformly distributed throughout 2000 to 20,000 parts, by weight, of an excipient capable of binding said steroidal medicinal agent to an extent greater than 80% and a demixing potential of less than 10% for said steroidal medicinal agent, in the form of tablets, capsules or slugged granulates, wherein said excipient is selected from a spray-dried polyalcohol, granulated α-lactose monohydrate, or mixtures thereof.

4. The pharmaceutical dosage unit of claim 3, wherein said medicinal agent is selected from desogestrel, 3-ketodesogestrel, ethinylestradiol, gestodene, or mixtures thereof.

5. The pharmaceutical dosage unit of claim 3, wherein the excipient is spray-dried lactose.

6. A process of making pharmaceutical dosage units containing at least one micronized steroidal medicinal agent present in an amount varying from 0.005 to 0.5 percent by weight of each pharmaceutical dosage unit comprising: dry mixing 1 to 100 parts, by weight, of said steroidal medicinal agent with 2000 to 20,000 parts, by weight, of an excipient capable of binding said steroidal medicinal agent to an extent greater than 80% and a demixing potential of less than 10% for said steroidal medicinal agent and forming the admixture into a dosage unit selected from the group consisting of tablets, capsules and slugged granulates.

7. The process according to claim 6 further comprising: adding further excipients for direct compression, in an amount of up to nine times the weight of the medicinal agent/excipient mixture to form an admixture containing 0.005 to 0.5% medicinal agent by weight.

8. The process of claim 6 further comprising: compressing the admixture into tablets containing less than 0.5 percent medicinal agent by weight.

9. The process of claim 7 further comprising: compressing the admixture into tablets containing less than 0.5 percent medicinal agent by weight.

10. The process according to claim 6 wherein said excipient having a binding affinity greater than 80% and demixing potential less than 10% for the steroidal medicinal agent is selected from a spray-dried polyalcohol, granulated α-lactose monohydrate or mixtures thereof.

11. The process of claim 6 wherein said medicinal agent is selected from desogestrel, 3-ketodesogestrel, ethinylestradiol, gestodene, or mixtures thereof.

12. A process of making pharmaceutical dosage units containing at least one micronized steroidal medicinal agent present in an amount varying from 0.005 to 0.5 percent by weight of each pharmaceutical dosage unit, comprising:

dry mixing 1 to 100 parts, by weight, of said steroidal medicinal agent with 2000 to 20,000 parts, by weight, of an excipient capable of binding said steroidal medicinal agent to an extent greater than 80% and a demixing potential of less than 10% for said steroidal medicinal agent; and forming the admixture into a dosage unit selected from the group consisting of tablets, capsules and slugged granulates, wherein said excipient is selected from a spray-dried polyalcohol, granulated α-lactose monohydrate, or mixtures thereof.

13. The process according to claim 12, further comprising: adding further excipients for direct compression in an amount of up to nine times the weight of the medicinal agent/excipient mixture to form an admixture containing 0.005 to 0.5% medicinal agent by weight.

14. The process of claim 12, further comprising: compressing the admixture into tablets containing less than 0.5% medicinal agent by weight.

15. The process of claim 13, further comprising: compressing the admixture into tablets containing less than 0.5% medicinal agent by weight.

16. The process of claim 12, wherein the excipient is spray-dried lactose.

17. The process of claim 12, wherein said medicinal agent is selected from desogestrel, 3-ketodesogestrel, ethinylestradiol, gestodene, or mixtures thereof.

18. A process of manufacturing tablets characterized in that the resulting tablets have an amount of steroidal medicinal agent which is within 4 percent relative standard deviation of all the tablets produced by that process comprising:

dry mixing 1 to 100 parts, by weight, of said steroidal medicinal agent with 2000 to 20,000 parts, by weight, of an excipient capable of binding said steroidal medicinal agent to an extent greater than 80% and a demixing potential of less than 10% for said steroidal medicinal agent, adding further excipients for direct compression, in an amount of up to nine times the weight of the medicinal agent/excipient mixture to form an admixture containing 0.005 to 0.5% medicinal agent by weight, and compressing the admixture into tablets containing less than 0.5 percent medicinal agent by weight.

* * * * *